(12) United States Patent
Greenlee (10) Patent No.: US 7,179,298 B2
(45) Date of Patent: Feb. 20, 2007

(54) HIP PROSTHESIS AND THE USE THEREOF

(76) Inventor: Wilfred E. Greenlee, 4423 Eagles Cove Ct., Louisville, KY (US) 40241-4802

( * ) Notice: Subject to any disclaimer, the term of this patent is extended or adjusted under 35 U.S.C. 154(b) by 0 days.

(21) Appl. No.: 10/908,841

(22) Filed: May 27, 2005

(65) Prior Publication Data

US 2006/0271200 A1  Nov. 30, 2006

(51) Int. Cl.
A61F 2/32 (2006.01)

(52) U.S. Cl. .................................. 623/22.16

(58) Field of Classification Search .... 623/22.13–22.2, 623/FOR. 19, FOR. 23
See application file for complete search history.

(56) References Cited

U.S. PATENT DOCUMENTS

| | | | |
|---|---|---|---|
| 3,723,995 A | 4/1973 | Baumann | |
| 3,916,451 A | 11/1975 | Buechei et al. | |
| 4,129,903 A | 12/1978 | Huggler | |
| 4,172,296 A | 10/1979 | D'Errico | |
| 4,714,477 A | 12/1987 | Fichera et al. | |
| 4,770,659 A | 9/1988 | Kendall | |
| 4,795,471 A | 1/1989 | Oh | |
| 4,842,605 A | 6/1989 | Sonnerat et al. | |
| 4,957,510 A | 9/1990 | Cremascoli | |
| 5,030,238 A | 7/1991 | Nieder et al. | |
| 5,092,898 A | 3/1992 | Bekki et al. | |
| 5,507,818 A | 4/1996 | McLaughlin | |
| 5,556,434 A | 9/1996 | Epstein | |
| 5,593,445 A | 1/1997 | Waits | |
| 5,725,597 A | 3/1998 | Hwang | |
| 5,800,556 A * | 9/1998 | Sanders et al. | 623/22.45 |
| 5,800,558 A | 9/1998 | LaHaise, Sr. | |
| 5,888,207 A | 3/1999 | Nieder et al. | |
| 6,328,764 B1 | 12/2001 | Mady | |
| 2004/0068322 A1* | 4/2004 | Ferree | 623/23.39 |
| 2004/0193282 A1 | 9/2004 | Hanes | |

FOREIGN PATENT DOCUMENTS

| | | | |
|---|---|---|---|
| BR | PI 9606183-9 A | * | 9/1998 |
| CN | 1481766 A | * | 3/2004 |
| EP | 0481855 A1 | | 4/1992 |
| EP | 1 350 486 A1 | * | 10/2003 |
| FR | 2705883 A1 | | 12/1994 |
| WO | WO 89/11837 A1 | * | 12/1989 |

OTHER PUBLICATIONS

PROFEMUR Total Hip System (technical monograph), Wright Medical Technology, Inc., Arlington, TN 38002 (2003); 11 pages.*

(Continued)

Primary Examiner—David H. Willse (57) ABSTRACT

Hip prosthesis. The femur side hip prosthesis includes both a ball and socket bearing and another (secondary) bearing system which facilitates motion of the type which is primarily in the forward and backward swinging of the leg. In certain embodiments of the invention, the secondary bearing system includes needle bearings and thrust bearings. That secondary bearing system lessens the motion of the ball and socket joint required during common activities such as walking. Certain embodiments of the invention include a modular connection between the stem for placement within the femur and the assembly that includes the secondary bearing.

32 Claims, 6 Drawing Sheets

OTHER PUBLICATIONS

Amstutz HC, Contini R, Johnson RL. *Biomechanical considerations of multiple-component hip prostheses. Analysis of three failures of the Lippman transfixation hip prosthesis*. Clinical orthopaedics and related research. (1975) 106:131-9.

de Jong PT, van der Vis HM, de Man FH, Marti RK. *Weber rotation total hip replacement: a prospective 5- to 20-year followup study*. Clinical orthopaedics. (2004) 419:107-14.

Christiansen T. *A combined endo- and total hip prosthesis with trunnion-bearing. The Christiansen prosthesis*. Acta chirurgica Scandinavica. (1974) 140:185-8.

Sundal B, Kavlie H, Christiansen T. *Total hip replacement with a new trunnion-bearing prosthesis (the Christiansen prosthesis). A report on the prosthesis and the early results*. Acta chirurgica Scandinavica. (1974) 140:189-93.

Weber BG. *Total hip replacement with rotation-endoprosthesis. [Trunnion-bearing prosthesis]*. Clinical orthopaedics and related research. (1970) 72:79-84.

Meyer S. *Prosthetic replacement in hip fractures: a comparison between the Moore and Christiansen endoprostheses*. Clinical orthopaedics and related research. (1981) 160:57-62.

Wright Medical Technology, Inc. "Profemur™ Modular Neck" (Technical Monograph) date 2003 Wright Medical Technology, Inc. Arlington, TN U.S.A, 11 pages.

* cited by examiner

Fig. 6

HIP PROSTHESIS AND THE USE THEREOF

CLARIFICATIONS ABOUT SELECTED TERMS

The term "prosthetic implant" is commonly used to refer not only to the item once implanted, but also to the item intended for implantation. That comprehensive meaning is embraced here.

In prostheses with ball and socket joints, the ball and socket system is referred to here as the "primary bearing system." In prostheses with both a ball and socket joint and another bearing system, the bearing system which is not the ball and socket system is referred to here as the "secondary bearing system." These terms are for convenience of reference, and do not imply relative degrees of importance, stress or motion.

BACKGROUND OF THE INVENTION

Hip joint deterioration frequently leads to patients undergoing total hip replacement (total hip arthroplasty). Such hip joint deterioration has many causes including, but not limited to, degenerative arthritis, rheumatoid arthritis, ankylosing spondylitis, avascular necrosis (both primary and secondary), osteoarthritis (both primary and secondary), ankylosis secondary to previous infections, spontaneous ankylosis, postsurgical ankylosis, bone tumors (both benign and malignant) around the hip joint, and hip fractures.

Approximately 193,000 total hip replacements were performed in the United States in 2002 (2002 National Hospital Discharge Survey, United States Department of Health and Human Services, Centers for Disease Control and Prevention, National Center for Health Statistics, May 21, 2004). Both the number of total hip replacements and the per capita rate of such operations have been increasing significantly.

During the decades that hip replacements have been performed, there have been many variations. The following description is for the typical, conventional hip replacement. No attempt is made here to include exhaustive detail of the conventional hip replacement or to describe the many variations. Such a hip replacement requires the removal of the head (ball) and neck of the femur. Then, the femur is reamed, and repeated broaching operations hollow out and clean approximately six inches of the interior of the proximal femur. The operations prepare the femur for the acceptance of a prosthetic implant that has a ball attached. The prosthetic implant stem portion is designed to fit the last broach that hollows out the upper interior of the femur. The worn cartilage and arthritic condition in the socket area in the hip is machined out to a hemispherical shape for the acceptance of a titanium alloy part that is secured in position with one or more screws. A plastic liner is then fit into the titanium part. Then, the ball on the prosthetic implant of the femur is inserted into the plastic socket prosthetic implant prepared in the hip bone.

There are a large number of variations in conventional stem-and-ball femur-side prosthetic implants. In some cases each prosthetic implant is a single piece; in some cases the "stem" and "ball" are two pieces which are attached. In some cases the prosthetic implant is cemented; in some cases it is not. Various materials have been used (e.g., various alloys, ceramics). Stem length in those prosthetic implants varies considerably. The specific geometries vary (e.g., curvature of the stem). Ball size of those prosthetic implants varies considerably.

Although total hip arthroplasty is major surgery, the operations are sufficiently common and usually successful that one could use the term "routine." While the usual outcome of total hip arthroplasty is highly successful, the functional lifespan of the prostheses is often shorter than the life of the person into whom the prostheses are placed. The circumstance of people outliving their hip prostheses can result in additional surgeries to repair or replace the prostheses. Concerns about prostheses wearing out have been addressed numerous ways. Those include employment of materials and surface treatments intended to reduce wear. Attempts to prolong prosthesis life have also included employment of femur-side prosthesis equipped with a secondary bearing system in addition to the primary bearing system.

Veterinary total hip replacements are also performed. For animals with hip joints with similar mechanics to humans, the nature of the hip replacement procedure and the prosthetic implants used are similar to those used in humans.

SUMMARY OF THE INVENTION

One object of the invention disclosed here is to lessen the motion of the ball and socket joint required during common activities, thereby reducing the wear of the prosthesis parts. However, it is important that that object be accomplished while allowing the full range of motion afforded by a ball and socket joint. Reducing wear is particularly important given the biological effects of wear debris. The wear debris of a conventional hip prosthesis is known to trigger inflammatory responses, which, among other things, can contribute to further deterioration of the prosthesis.

The invention disclosed here is a femur side hip prosthesis having a secondary bearing system in addition to the primary bearing system. That secondary bearing system facilitates motion of the femur that is, generally speaking, involved in swinging the leg frontward and rearward. It is designed to be used in conjunction with a pelvis-side prosthesis similar to those conventionally used. This arrangement allows motion by way of the primary bearing system (in the conventional ball and socket manner) and, additionally, the freedom to rotate by way of the secondary bearing system. The degree of freedom afforded by this secondary bearing system allows the primary bearing system to undergo far less motion during certain common activities such as walking in a straight line. However, for leg actions requiring motions not fully accommodated by the rotation about the secondary bearing system, the primary bearing system can supply the needed freedom.

DETAILED DESCRIPTION OF SPECIFIC EMBODIMENTS

Embodiment I and Embodiment II of the invention disclosed here are described below. They are similar to each other. The principle difference is that in Embodiment II of the invention disclosed here there is a modular connection between the stem for placement within the femur and the assembly that includes the secondary bearing.

Figure 1:
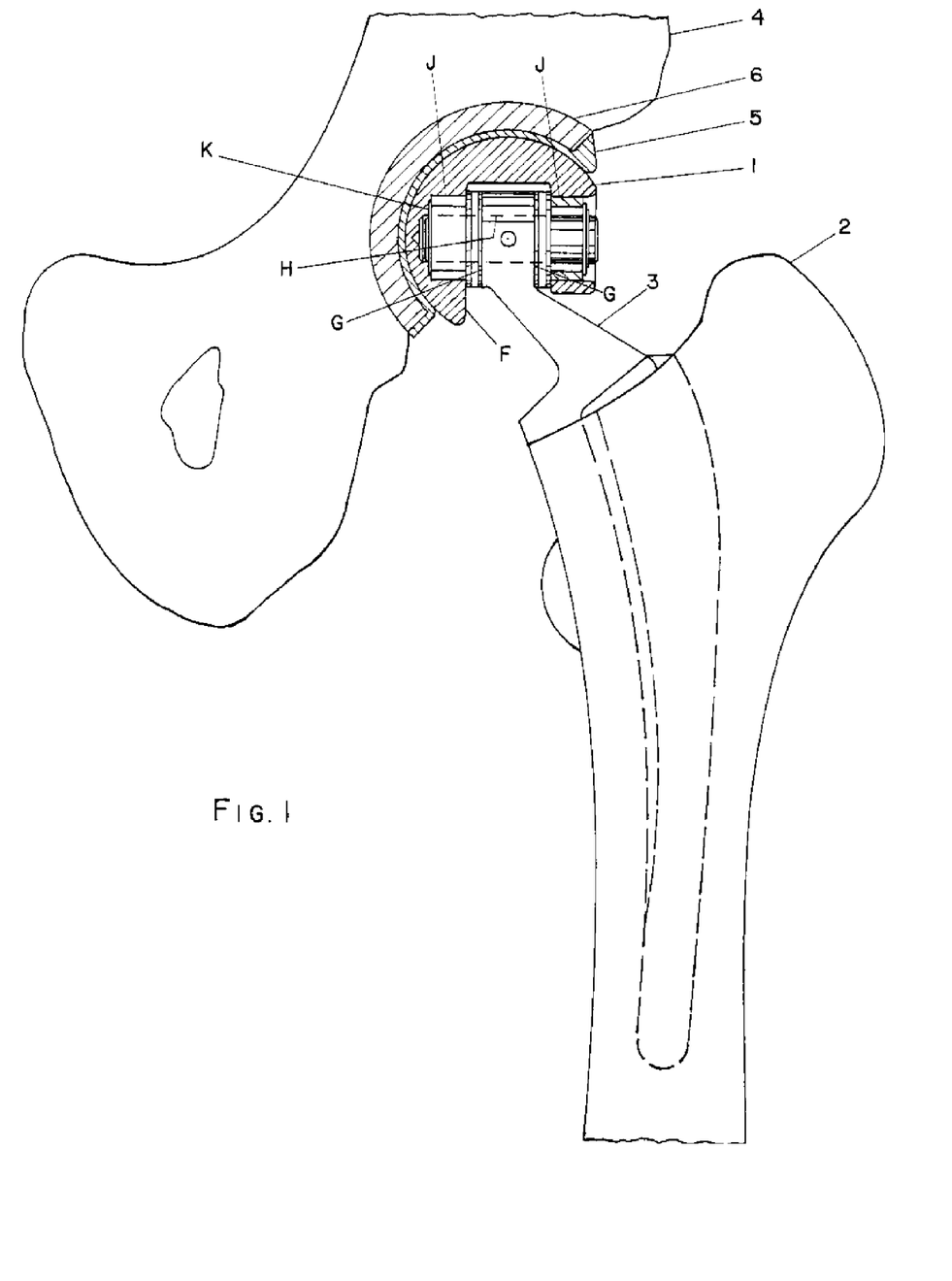
FIG. 1 is a partially cross-sectional depiction of Embodiment I of the invention disclosed here in a context which includes the proximal end of the femur, part of the pelvis and the prosthetic socket parts. More particularly, the pelvis, the primary bearing system and the secondary bearing system are shown in cross-section. The view is an anterior view of the left hip.

FIG. 1 is a partially cross-sectional depiction of Embodiment I of the invention disclosed here. More particularly, the pelvis, the primary bearing system and the secondary bearing system are shown in cross-section. The view is an anterior view of the left hip. FIG. 1 will be used in describing the general features of Embodiment I of the invention disclosed here. In Embodiment I, the ball 1 interfaces with a socket liner 5 within an acetabulum shell prosthetic implant 6 which is secured within the pelvis 4.

Figure 4:
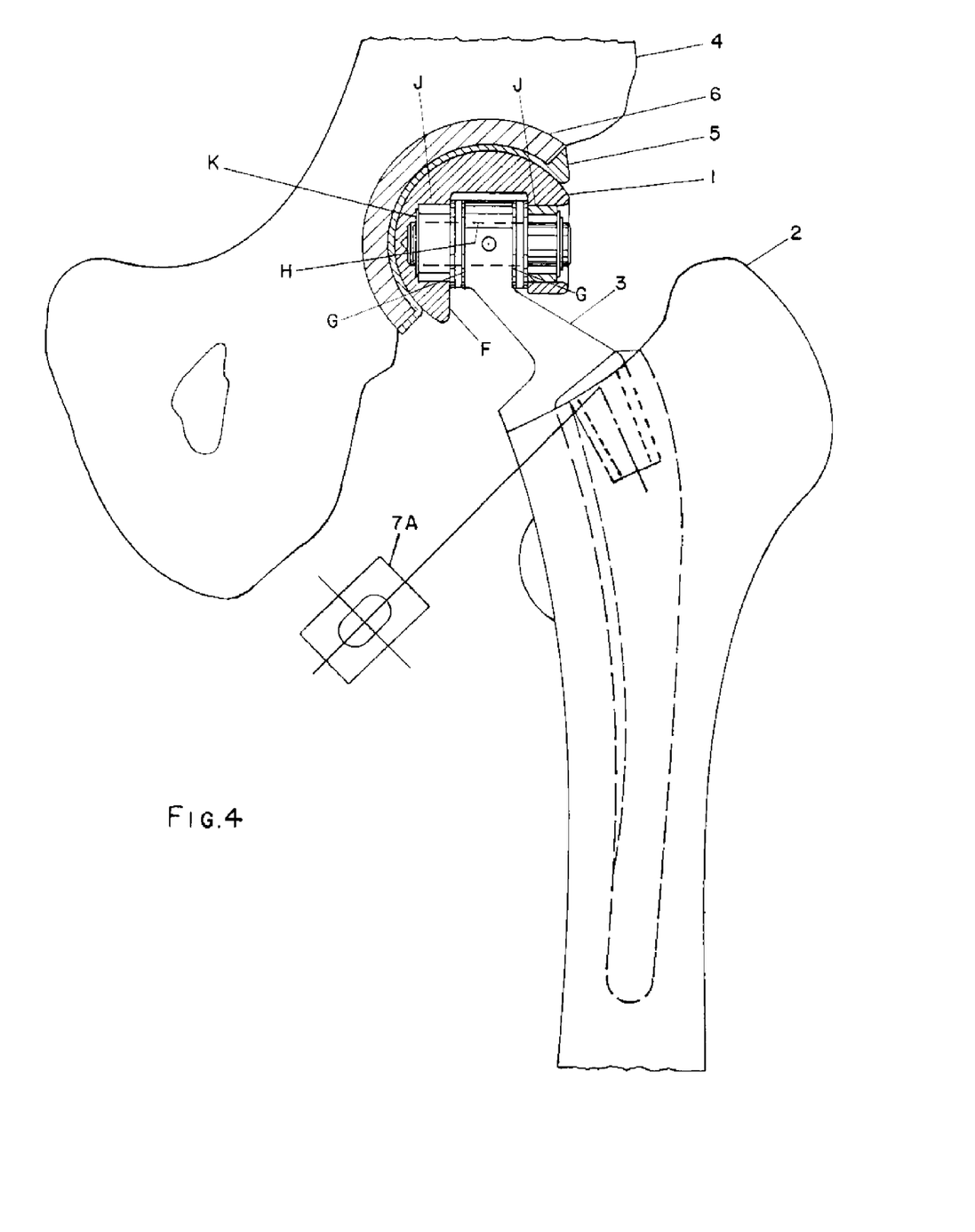
FIG. 4 is a partially cross-sectional depiction of Embodiment II of the invention disclosed here in a context which includes the proximal end of the femur, part of the pelvis and the prosthetic socket parts. More particularly, the pelvis, the primary bearing system and the secondary bearing system are shown in cross-section. The view is an anterior view of the left hip. The depiction is oriented the same way as FIG. 1. The cross-sectional shape of the modular connection is also indicated.

FIG. 4 is a partially cross-sectional depiction of Embodiment II of the invention disclosed here. More particularly, the pelvis, the primary bearing system and the secondary bearing system are shown in cross-section. The view is an anterior view of the left hip. The primary features that make Embodiment II of the invention disclosed here different from Embodiment I of the invention disclosed here are depicted on FIG. 4. As was true of FIG. 1 for Embodiment I, FIG. 4 for Embodiment II of the invention disclosed here depicts the ball 1, femur 2, pelvis 4, socket liner 5, and acetabulum shell prosthetic implant 6. As shown on FIG. 4, Embodiment II of the invention disclosed here has a part 3 that at one end is part of the secondary bearing system and at the other end is designed to be the male portion of a modular connection. That male connecting region is tapered and is an oval in cross-section. That male portion is intended to connect with the stem implanted within the femur. The taper is self locking. That stem is equipped with a female connecting region with is complementary to the male connecting region. The shape of the opening of the female connection region is indicated 7A. This modular construction allows the replacement of the assembly which includes the bearings, if revision surgery is required, without the need to disturb the stem within the femur. Because of this, Embodiment II is preferred over Embodiment I for many applications.

The acetabulum shell prosthetic and socket liner are similar to those used in the conventional total hip replacement. The principle difference between the socket liner and acetabulum shell prosthetic implant intended to be used with Embodiment I and Embodiment II of the invention disclosed here, and the socket liner and acetabulum shell prosthetic implant used in conventional total hip replacement is that the socket liner and acetabulum shell prosthetic used with Embodiment I and Embodiment II of the invention disclosed here have a geometry which accommodates a larger ball than is conventionally used.

The preferred materials of the socket liner and the acetabulum shell prosthetic implant used in Embodiment I and Embodiment II of the invention disclosed here are similar to those used in the conventional total hip replacement. For example, the acetabulum shell prosthetic implant may be made primarily of a titanium shell with titanium metal fibers bonded to the pelvis-facing surfaces and the acetabulum socket liner may be made of ultra-high-molecular-weight polyethylene (UHMWPE).

Although other materials could be used, the preferred material for the ball member of Embodiment I and Embodiment II of the invention disclosed here is cobalt chromium steel. The preferred hardness of the steel is between 30 and 40 Rc. The ball member is machined from a ball with a diameter of 1.62500±0.00002 inches and a sphericity ≦0.00004 inches.

The acetabulum shell prosthetic and socket liner are surgically installed essentially as those parts are installed in conventional total hip replacement. Referring to FIG. 1 in the case of Embodiment I of the invention disclosed here and FIG. 4 in the case of Embodiment II, the stem of the prosthesis 3 is essentially the same as those of conventional femur side prostheses for total hip replacement. In fact, the range of variations in specific materials and geometry for stems conventionally used would be possible with this invention. Likewise, the femur 2 is prepared (broached and reamed) in the manner of the conventional total hip replacement. The secondary bearing system is disposed between the stem that anchors the prosthesis into the femur and the ball that is a component of the primary bearing system. Ideally, the femur side installation would align the cross shaft of the secondary bearing system so that, while standing, it would be nearly perpendicular to a straight line struck from the center line of the ball through the centerline of the ankle joint axis, and would also be nearly parallel with the oblique diameter of the pelvis.

Figure 3:
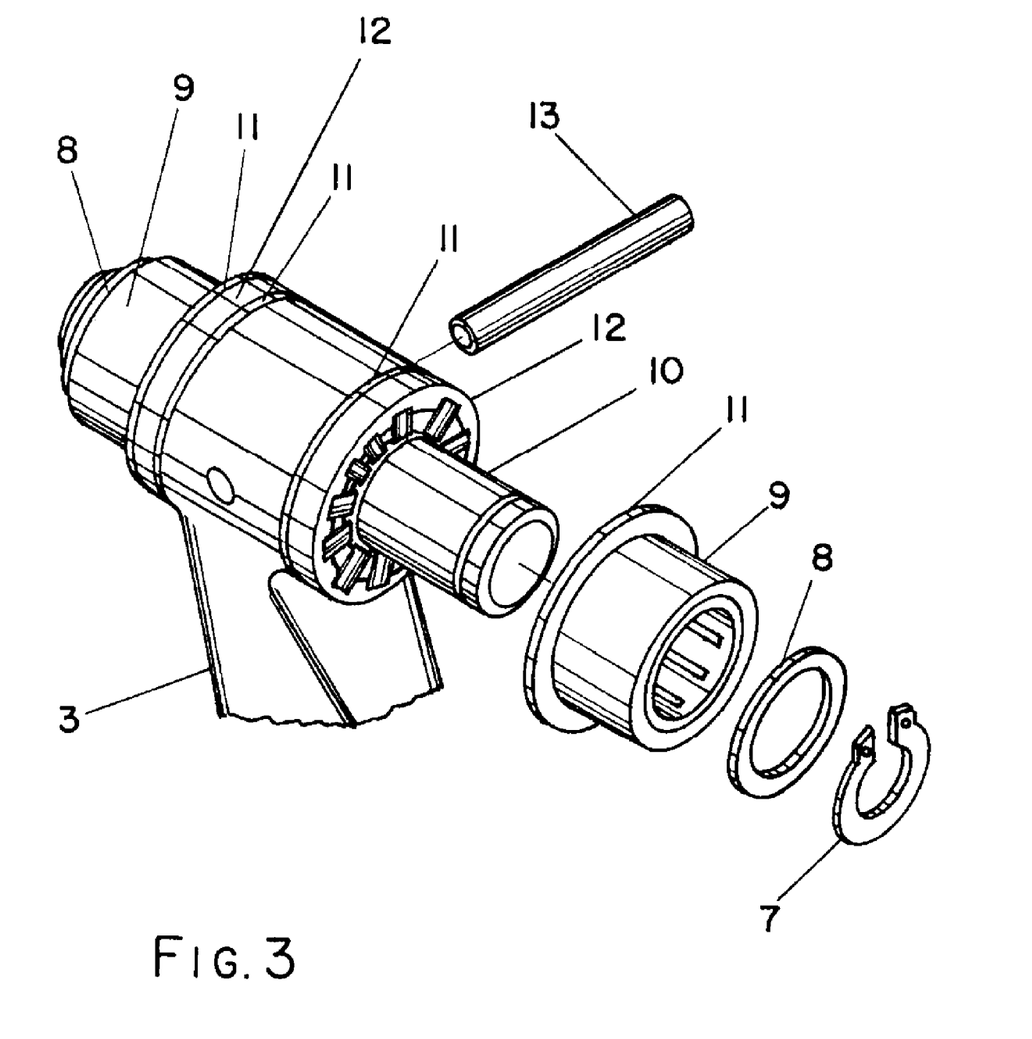
FIG. 3 is a partially exploded isometric depiction of the bearing mechanism of Embodiment I and Embodiment II of the invention disclosed here.

FIG. 3 shows more detail of the secondary bearing system of both Embodiment I and Embodiment II of the invention disclosed here. That secondary bearing system includes a cross shaft 10, two hardened precision washers 8, two needle bearing assemblies 9, four hardened precision thrust bearing races 11, two thrust needle bearings 12 and a roll pin 13.

Variations on the specific configuration of the secondary bearing system are possible and may be preferable for some circumstances. By way of illustration, alternative embodiments include those that use loose-roller type roller bearings instead of retained roller type roller bearings found in Embodiment I and Embodiment II. By way of another example, embodiments could lack the thrust bearings.

Referring to FIG. 1 for Embodiment I and FIG. 4 for Embodiment I, the width of the interior face of the ball F to the opposite face of the interior of the ball is 0.672 inches. The roll pin has a 0.125 inch diameter and is 0.750 inches long. The cross shaft has a 0.375 inch diameter.

In Embodiment I and Embodiment II, the roll pin secures the ball of the prosthesis to the secondary bearing mechanism. Referring to FIG. 3, the snap ring 7 secures the hardened precision washers, needle bearing assemblies, four hardened precision thrust bearing races, and thrust needle bearings on the cross shaft.

In Embodiment I and Embodiment II of the invention disclosed here, the ball being larger than in conventional total hip replacement somewhat increases the friction of the primary joint. That is advantageous because it causes there to be more friction resisting the motion of the primary bearing system than friction resisting the motion of the secondary bearing system. That causes most of the motion that can be accommodated by the secondary bearing system to be so accommodated, eliminating unnecessary motion of the primary bearing system. That in turn, lessens wear of the primary bearing system.

Referring to FIG. 1 in the case of Embodiment I, and FIG. 4 in the case of Embodiment II, the two neck faces G, the end face K and interior face F are all parallel to each other and perpendicular to the cross shaft bore H. Each of those two parallel faces G neighbor a thrust bearing assembly consisting of a thrust bearing and two hardened precision thrust bearing races. The two needle bearings j and the thrust bearings all share an axis of rotation which is a diameter of the ball member. The width between face F and the opposite face is 0.6720±0.0005 inches.

Figure 5:
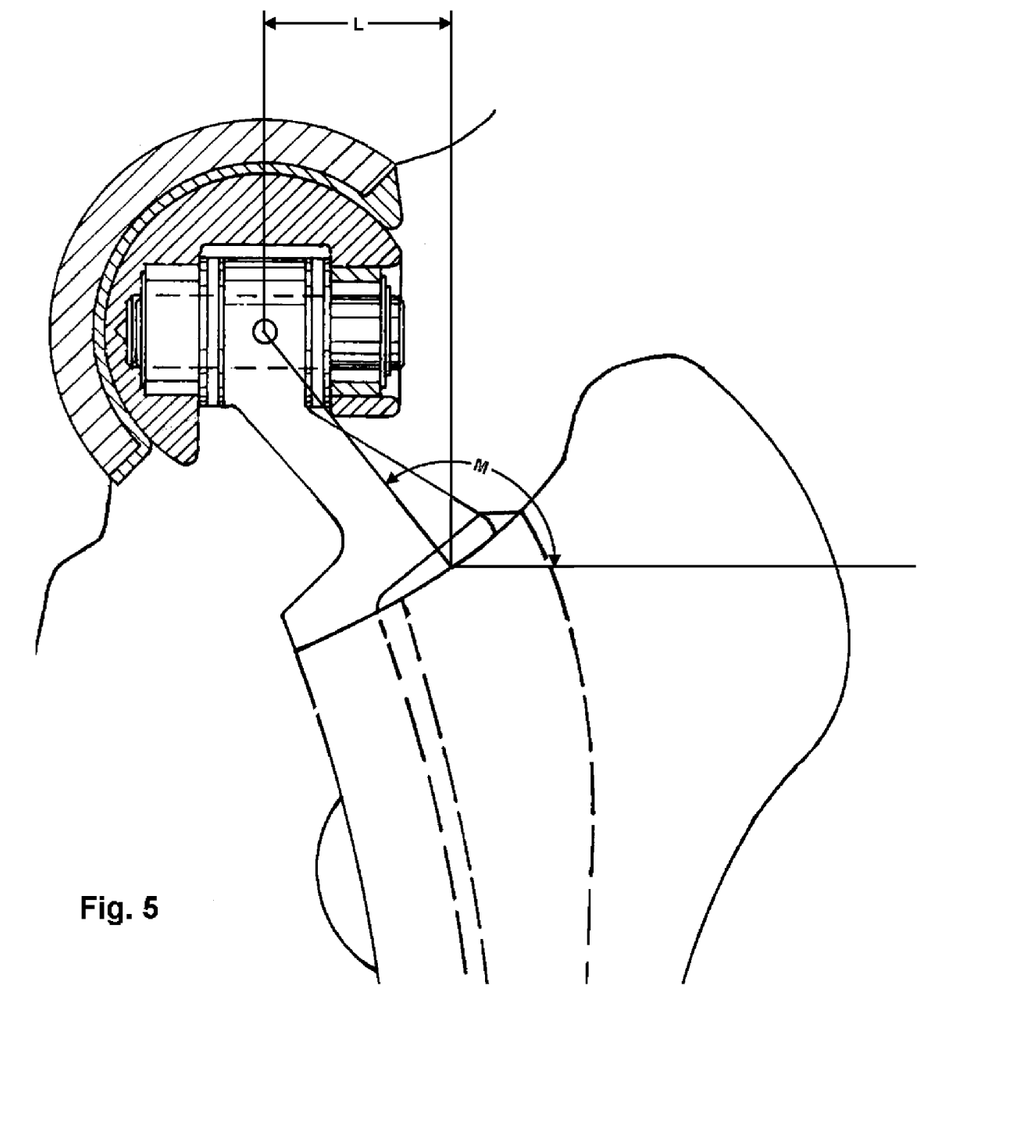
FIG. 5 indicates a certain angle and length on Embodiment I of the invention disclosed here. The view is an anterior view of the left hip. The depiction is oriented the same way as FIG. 1.
Figure 6:
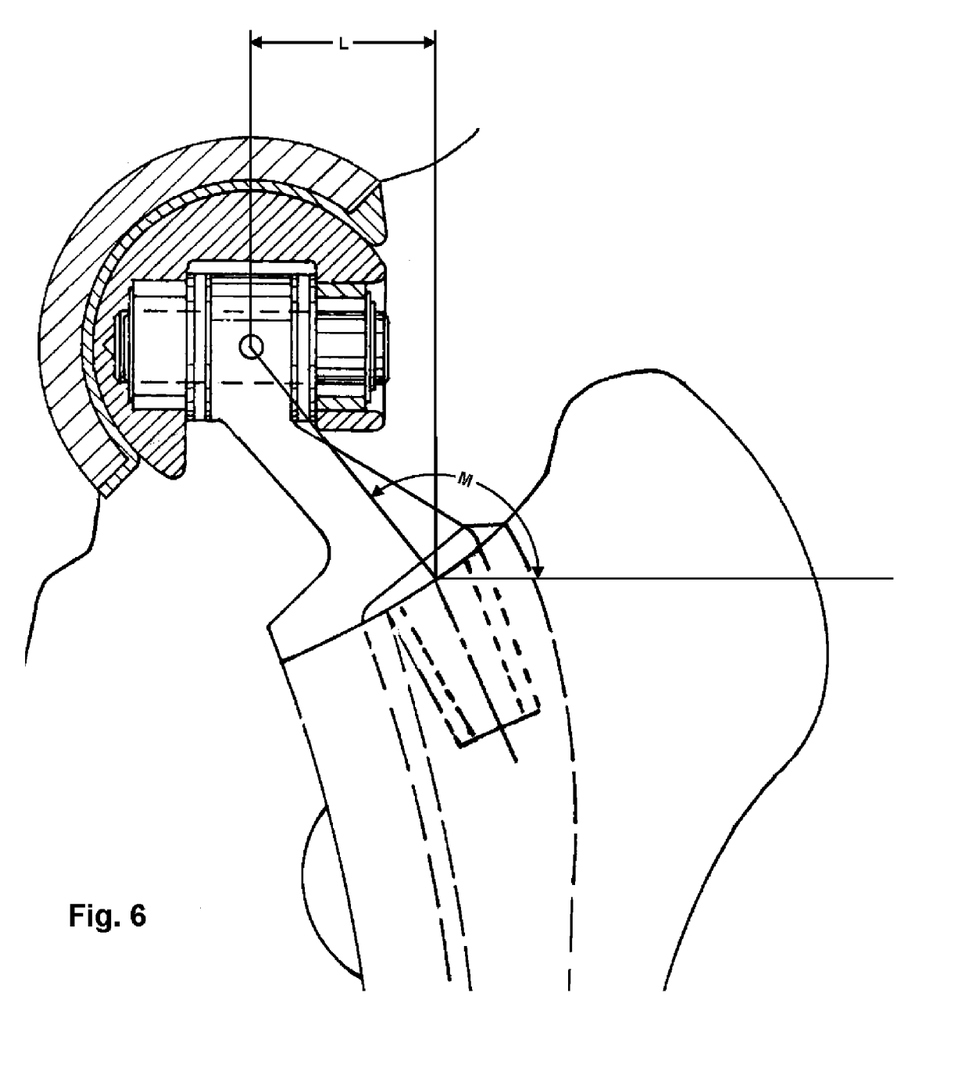
FIG. 6 indicates a certain angle and length on Embodiment II of the invention disclosed here. The view is an anterior view of the left hip. The depiction is oriented the same way as FIG. 1. The cross-sectional shape of the modular connection is also indicated.

For both Embodiment I and Embodiment II, it would be preferred that the prosthesis be available to surgeons in a variety of angles and lengths allowing the geometry to be optimized for each patient. For example, for Embodiment I of the invention disclosed here it would be preferred if the part identified as 3 on FIG. 1 be supplied in a variety of values for length L and angle M as indicated on FIG. 5. As another example, for Embodiment II of the invention disclosed here it would be preferred if the part identified as 3 on FIG. 4 be supplied in a variety of values for length L and angle M as indicated on FIG. 6. In each of those examples, L is the horizontal component of the distance between the center point of the stem of the prosthesis at its entry into the femur and the center point of the ball member of the prosthesis. In each of those examples, M is the angle between a particular line segment and a particular ray. That line segment runs between the center point of the stem of the prosthesis at its entry into the femur and the center point of the ball member of the prosthesis. The ray starts at the center point of the stem of the prosthesis at its entry into the femur, and is directed out of the body (on the same side of the body as the hip is located) parallel with the centerline of the cross-shaft.

After implantation, the functioning of Embodiment I and Embodiment II of the invention would be essentially the same. When the femur is moved relative to the pelvis in a manner that can be fully accommodated by the secondary bearing system, the motion would be so accommodated with the primary bearing system remaining static or nearly so. When the femur is moved relative to the pelvis in a manner which cannot be fully accommodated by the secondary bearing system, the motion will be accommodated by the secondary bearing system to the extent possible, with the primary bearing system accommodating the motion not accommodated by the primary bearing system.

The specific example of walking is of particular importance, because in many people who undergo total hip replacement, it is the cause of the majority of the wear on the prosthetic bearing. For Embodiment I of the invention disclosed here or Embodiment II of the invention disclosed here, when one is walking straight, the majority of the motion of the femur relative to the pelvis would be accommodated by the secondary bearing system with the primary bearing system moving only a little (e.g., to accommodate the "roll" of the hip that occurs during walking). The ideal alignment of the cross shaft (discussed above) would minimize the motion needed to be accommodated by the primary bearing system during normal walking. If the actual alignment was not ideal, there would be somewhat increased motion of the primary bearing system during walking. While that would somewhat increase wear of that primary bearing system, the motion could be accommodated.

Figure 2:
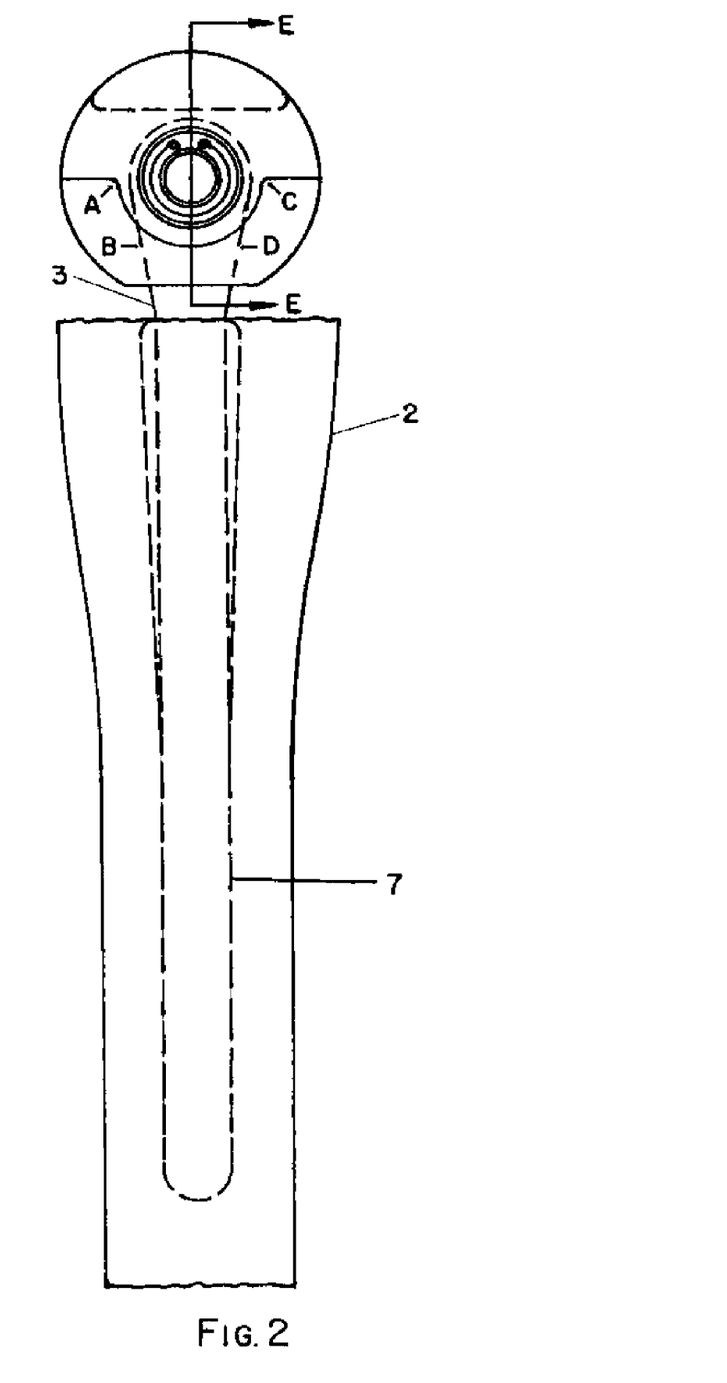
FIG. 2 depicts Embodiment I of the invention disclosed here in a context which includes the femur. The orientation of the invention depicted in FIG. 2 is orthogonal to the orientation depicted in FIG. 1. Markings E in FIG. 2 indicate the orientation of the cross-sectional view in FIG. 1 and FIG. 4.

Another specific example of motion, sitting, will be used to illustrate the function of Embodiment I and Embodiment II of the invention disclosed here. FIG. 2 depicts Embodiment I of the invention disclosed here in that the modular connection of Embodiment II of the invention disclosed here is not present. However, the mechanics discussed in this and the immediately following paragraph would generally apply to Embodiment I and Embodiment II. For this example it will be assumed that immediately prior to the sitting action, the secondary bearing system is aligned as depicted in FIG. 2. At the start of sitting action, the movement of the femur relative to the pelvis would be accommodated by the secondary bearing system. Referring to FIG. 2, approximately half way through the sitting action, point C on the ball and point D on the stem of the prosthesis will contact. That will prevent the secondary bearing from accommodating the remainder of the sitting action. From then until the end of the sitting action, the motion of the femur relative to the pelvis will be accommodated by the primary bearing. The mechanics of the prosthesis during sitting action would be very similar for Embodiment II of the invention disclosed here.

Looking now at the specific example of standing from a seated position. If the person who sat in the example in the immediately proceeding paragraph now stands, nearly the entire motion of the femur relative to the pelvis can be accommodated by the secondary bearing. That is because, if at the beginning of the standing action point C on the ball and point D on the stem of the prosthesis are in contact, 90° of rotation is possible before point A on the ball and point B on the stem of the prosthesis make contact.

The prosthetic implants and the use of those prosthetic implants disclosed here can be applied to the right and the left hip joints.

The class of prosthetic implants and the use of those prosthetic implants disclosed here can be applied to human hips and to the hips of other animals with ball-and-socket hip joints. For animals other than humans, the prosthetic system would need to be adapted, for instance, by appropriate sizing of parts.

From the above description and drawings, it will be understood by those of ordinary skill in the art that the particular embodiments shown and described are for purpose of illustration only, and are not intended to limit the scope of the invention. Those of ordinary skill in the art will recognize that the invention may be embodied in other specific forms without departing from its spirit or essential characteristics. References to details of particular embodiments are not intended to limit the scope of the claims.

What is claimed is:

1. A hip prosthetic system for implantation in a patient's body, said system comprising:
   a.) an intramedullary stem;
   b.) a primary bearing system comprising a socket component and a ball component having a bearing surface generally defining a majority of a sphere;
   c.) a secondary bearing system including at least one antifriction thrust bearing and defining an axis of rotation oriented relative to said intramedullary stem such that upon implantation, said axis of rotation is substantially perpendicular to a line extending from a center of said ball component to a center of the corresponding ankle joint while the patient is standing.

2. The hip prosthetic system of claim 1, wherein said secondary bearing system comprises a cross shaft extending along said axis of rotation.

3. The hip prosthetic system of claim 1, wherein said ball component is machined from a ball with a diameter of 1.62500±0.00002 inches.

4. The hip prosthetic system of claim 1, wherein said ball component comprises a biocompatible metal or metal alloy.

5. The hip prosthetic system of claim 4, wherein said metal or metal alloy comprises cobalt chromium steel.

6. The hip prosthetic system of claim 1, wherein said system comprises a plurality of intramedullary stems and femoral necks oriented relative to respective stems at a variety of angles so as to accommodate a range of patients.

7. The hip prosthetic system of claim 1, further comprising a femoral neck which includes an integrally formed portion generally centered within said ball component and having a cross-shaft bore, said femoral neck extending generally inferiorly and laterally from said integrally formed portion for attachment to said intramedullary stem.

8. The hip prosthetic system of claim 1, further comprising a modular neck component having a self-locking taper configured to engage a female connecting region in said intramedullary stem.

9. The hip prosthetic system of claim 1, wherein said secondary bearing system comprises a cross shaft and a plurality of needle bearings.

10. The hip prosthetic system of claim 9, wherein said bearings comprise loose-roller type bearings configured to impart reduced friction in a physiological environment.

11. The hip prosthetic system of claim 1, further comprising a roll pin to secure said ball component to said secondary bearing system.

12. The hip prosthetic system of claim 1, wherein said hip prosthetic system is configured to be implanted in a human.

13. The hip prosthetic system of claim 1, wherein said hip prosthetic system is configured to be implanted in an animal other than a human.

14. The hip prosthetic system of claim 1, wherein said bearing surface of said ball component is essentially a single piece of material.

15. The hip prosthetic system of claim 1, wherein said axis of rotation of said secondary bearing system is approximately perpendicular to an overall orientation of said intramedullary stem.

16. The use in a human or animal of the hip prosthetic system of claim 1, comprising resecting a head and neck portion of a femur in said human or animal, creating a cavity generally along the medullary canal of the femur, and inserting said prosthetic system into the medullary canal.

17. A hip prosthetic system for implantation in a patient's body, said system comprising:
  a.) an intramedullary stem;
  b.) a primary bearing system comprising a socket component and a ball component, said ball component having a socket facing side comprising a bearing surface, said socket facing side being devoid of any openings;
  c.) a secondary bearing system defining an axis of rotation oriented generally perpendicular to a plumb line while the patient is standing and configured to facilitate motion of a femur involved in swinging a leg forward and backward and minimize movement of said ball and socket components, with said primary bearing system providing the needed freedom for leg actions requiring motions not fully accommodated by said secondary bearing system, wherein said secondary bearing system includes an antifriction thrust bearing.

18. The hip prosthetic system of claim 17, wherein said ball component is of a size sufficient to increase somewhat the friction in said primary bearing system such that a majority of the motion is accommodated by said secondary bearing system so as to reduce wear of said ball and socket components and thereby minimize wear debris and inflammatory responses.

19. The hip prosthetic system of claim 18, wherein said ball component is machined from a ball with a diameter of 1.62500±0.00002 inches.

20. The hip prosthetic system of claim 17, wherein said second bearing system comprises a range of rotation of at least 70°.

21. The hip prosthetic system of claim 17, wherein said second bearing system comprises a plane of rotation within 200 of parallel with the sagittal plane of the patient's body.

22. The hip prosthetic system of claim 21, wherein said plane of rotation is within 12° of parallel with the sagittal plane of the patient's body.

23. The hip prosthetic system of claim 17, wherein said hip prosthetic system is configured to be implanted in a human.

24. The hip prosthetic system of claim 17, wherein said hip prosthetic system is configured to be implanted in an animal other than a human.

25. A hip prosthetic system for implantation in a patient's body, said system comprising:
  a.) an intramedullary stem;
  b.) a primary bearing system comprising a socket component and a ball component having a bearing surface generally defining a majority of a sphere;
  c.) a secondary bearing system defining an axis of rotation oriented generally perpendicular to a plumb line while the patient is standing and configured to facilitate motion of a femur involved in swinging a leg forward and backward and minimize movement of said ball and socket components, with said primary bearing system providing the needed freedom for leg actions requiring motions not fully accommodated by said secondary bearing system, wherein said secondary bearing system includes an antifriction thrust bearing.

26. The hip prosthetic system of claim 25, wherein said ball component is of a size sufficient to increase somewhat the friction in said primary bearing system such that a majority of the motion is accommodated by said secondary bearing system so as to reduce wear of said ball and socket components and thereby minimize wear debris and inflammatory responses.

27. The hip prosthetic system of claim 26, wherein said ball component is machined from a ball with a diameter of 1.62500±0.00002 inches.

28. The hip prosthetic system of claim 25, wherein said second bearing system comprises a range of rotation of at least 70°.

29. The hip prosthetic system of claim 25, wherein said second bearing system comprises a plane of rotation within 200 of parallel with the sagittal plane of the patient's body.

30. The hip prosthetic system of claim 29, wherein said plane of rotation is within 12° of parallel with the sagittal plane of the patient's body.

31. The hip prosthetic system of claim 25, wherein said hip prosthetic system is configured to be implanted in a human.

32. The hip prosthetic system of claim 25, wherein said hip prosthetic system is configured to be implanted in an animal other than a human.

* * * * *